(12) United States Patent
Sakakibara et al.

(10) Patent No.: US 8,540,373 B2
(45) Date of Patent: Sep. 24, 2013

(54) RETINAL SCANNING DISPLAY

(75) Inventors: Masahiro Sakakibara, Toyokawa (JP); Norimi Yasue, Nagoya (JP)

(73) Assignee: Brother Kogyo Kabushiki Kaisha, Nagoya (JP)

( * ) Notice: Subject to any disclaimer, the term of this patent is extended or adjusted under 35 U.S.C. 154(b) by 285 days.

(21) Appl. No.: 12/891,077

(22) Filed: Sep. 27, 2010

(65) Prior Publication Data

US 2011/0075104 A1 Mar. 31, 2011

(30) Foreign Application Priority Data

Sep. 30, 2009 (JP) ................................ 2009-229098

(51) Int. Cl.
*G03B 21/28* (2006.01)
*G02B 26/08* (2006.01)
*G09G 5/00* (2006.01)
*G09G 3/00* (2006.01)

(52) U.S. Cl.
USPC ............... 353/31; 353/97; 359/198.1; 345/8; 345/32

(58) Field of Classification Search
USPC ................. 353/31, 97; 359/198.1; 345/7, 8, 345/32
See application file for complete search history.

(56) References Cited

U.S. PATENT DOCUMENTS

| 5,659,327 | A * | 8/1997 | Furness et al. ..................... 345/8 |
| 6,628,248 | B2 | 9/2003 | Masumoto et al. |
| 6,661,393 | B2 | 12/2003 | Tegreene et al. |
| 6,888,653 | B2 * | 5/2005 | Yamada et al. ............ 359/198.1 |
| 6,937,372 | B2 | 8/2005 | Kandori et al. |
| 2009/0096714 | A1 * | 4/2009 | Yamada ............................ 345/8 |
| 2009/0244407 | A1 * | 10/2009 | Sakakibara .................. 348/759 |
| 2011/0074837 | A1 | 3/2011 | Takeda et al. |

FOREIGN PATENT DOCUMENTS

| JP | A-2001-209342 | 8/2001 |
| JP | A-2003-025626 | 1/2003 |
| JP | A-2003-131151 | 5/2003 |
| JP | 2004-098472 | 4/2004 |
| JP | A-2004-184507 | 7/2004 |
| JP | A-2008-076562 | 4/2008 |
| JP | A-2008-89930 | 4/2008 |
| JP | A-2008-233562 | 10/2008 |
| JP | A-2009-069270 | 4/2009 |
| JP | A-2009-86371 | 4/2009 |

(Continued)

OTHER PUBLICATIONS

Nov. 13, 2012 Office Action issued in Japanese Patent Application No. 2009-229098 (with English-language translation).

(Continued)

*Primary Examiner* — Georgia Y Epps
*Assistant Examiner* — Magda Cruz
(74) *Attorney, Agent, or Firm* — Oliff & Berridge, PLC

(57) ABSTRACT

A retinal scanning display includes: a light source part which radiates a laser beam; a scanning part which scans the radiated laser beam in two dimensional directions; a projection part which projects the scanned laser beam on a retina of a viewer; a light detection part which is arranged at a position on which the scanned laser beam is incident; and a light blocking part which blocks the scanned laser beam scanned at the timing detection time; and a control part which controls the radiation of the laser beam based on the detected timing of the laser beam by the light detection part. The control part allows the light source part to radiate the laser beam at the timing detection time with intensity which exceeds a maximum value of intensity of the laser beam radiated from the light source part at the image forming time.

8 Claims, 10 Drawing Sheets

(56) References Cited

FOREIGN PATENT DOCUMENTS

| | | |
|---|---|---|
| JP | A-2011-075957 | 4/2011 |
| JP | A-2011-075958 | 4/2011 |

OTHER PUBLICATIONS

Mar. 12, 2013 Office Action issued in Japanese Patent Application No. 2009-229098 (with translation).

\* cited by examiner

RETINAL SCANNING DISPLAY

CROSS-REFERENCE TO RELATED APPLICATIONS

This application is based on and claims the benefit of priority from Japanese Patent Application No. 2009-229098 filed on Sep. 30, 2009, the entire contents of which are incorporated herein by reference.

BACKGROUND

1. Field

The present invention relates to a retinal scanning display.

2. Description of the Related Art

Conventionally, there has been known a retinal scanning display in which a laser beam having intensity corresponding to an image signal is scanned by a scanning part in two dimensional directions thus forming an image and the image is incident on a retina of a viewer who is a user so as to allow the viewer to recognize the image.

Among various types of retinal scanning displays, there has been known a retinal scanning display in which a light detection part is arranged on a scanning trajectory of a laser beam and a scanning position is obtained by detecting scanning timing of the laser beam by the light detection part thus enabling a control of radiation timing of a laser beam for forming an image (also referred to as "image light" hereinafter).

In such a retinal scanning display, a proper image light with respect to a scanning position of a scanning part can be radiated so that it is possible to prevent the occurrence of disturbance of an image which a viewer recognizes as much as possible.

SUMMARY OF THE INVENTION

In the above-mentioned conventional retinal scanning display, although the intensity of a laser beam incident on a retina of the viewer may be proper for an eye (retina) of the viewer, the intensity of the laser beam is too weak to a light detection part such as a BD sensor so that there has been a case where even when such a laser beam is incident on the light detection part, the accurate scanning timing cannot be obtained.

The present invention has been made in view of such circumstances, and it is an object of the present invention to provide a retinal scanning display which can overcome the shortage of light received by a light detection part thus preventing the occurrence of disturbance of an image as much as possible.

According to one aspect of the present invention, there is provided a retinal scanning display which includes: a light source part; a scanning part; a projection part; a light detection part; a light blocking part; and a control part.

Here, the light source part radiates a laser beam having intensity corresponding to a drive signal which includes an image signal. The scanning part scans the laser beam radiated from the light source part in two dimensional directions. The projection part, at image forming time, projects the laser beam which is radiated from the light source part and is scanned by the scanning part on a retina of an eye of a viewer thus projecting an image on the retina. The light detection part is arranged at a position on which the laser beam which is radiated from the light source part and is scanned by the scanning part at timing detection time at which scanning timing of the scanning part is detected other than the image forming time is incident.

The light blocking part is arranged between the scanning part and the viewer and is configured to block a laser beam which is scanned by the scanning part and advances toward the eye of the viewer at the timing detection time. The control part is configured to control the radiation of the laser beam from the light source part based on the detected timing of the laser beam by the light detection part. The control part also radiates the laser beam which is radiated from the light source part at the timing detection time with intensity which exceeds a maximum value of intensity of the laser beam which is radiated from the light source part at the image forming time.

DESCRIPTION

Hereinafter, a retinal scanning display (hereinafter, also referred to as "RSD") according to this embodiment is specifically explained in conjunction with drawings.

[1. Schematic Constitution of RSD]

Figure 1:
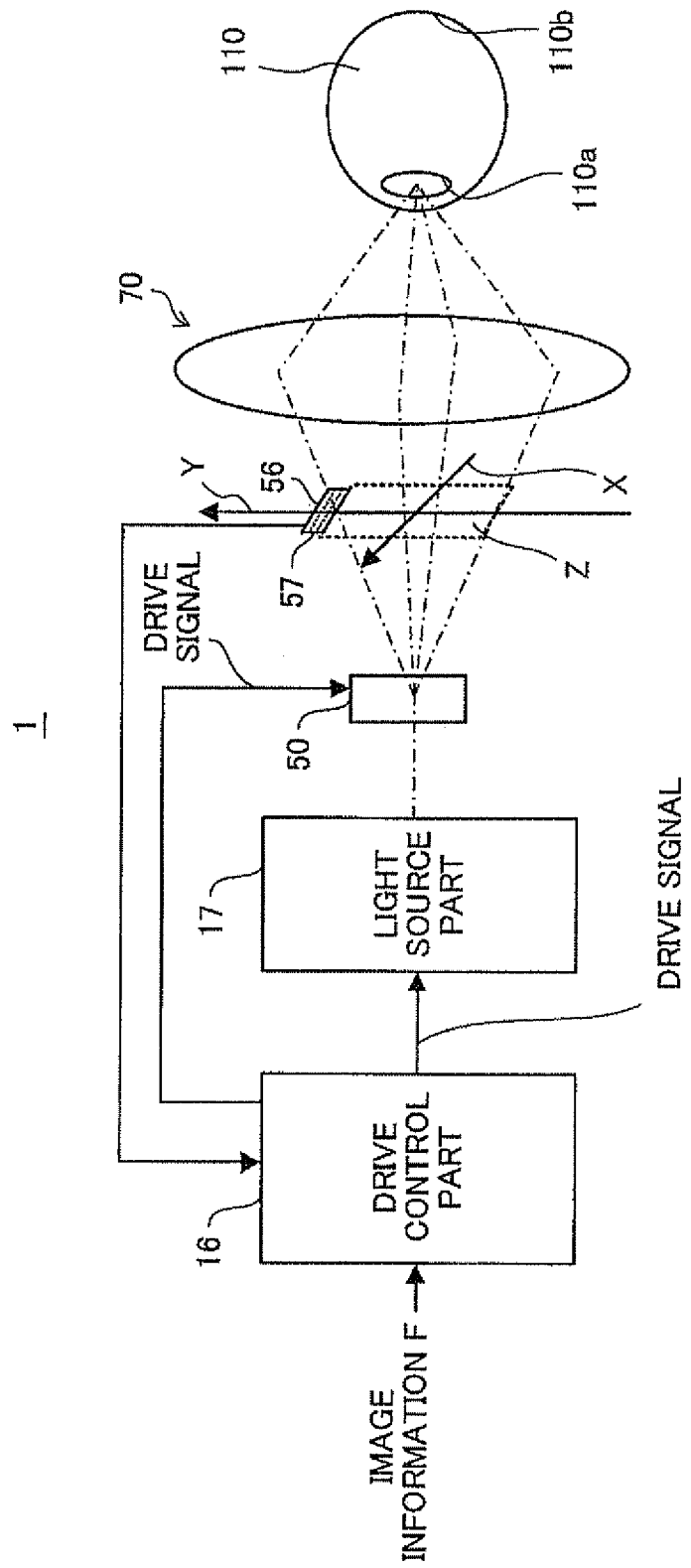
FIG. 1 is an explanatory view showing the appearance of a retinal scanning display according to an embodiment.
Figure 4:
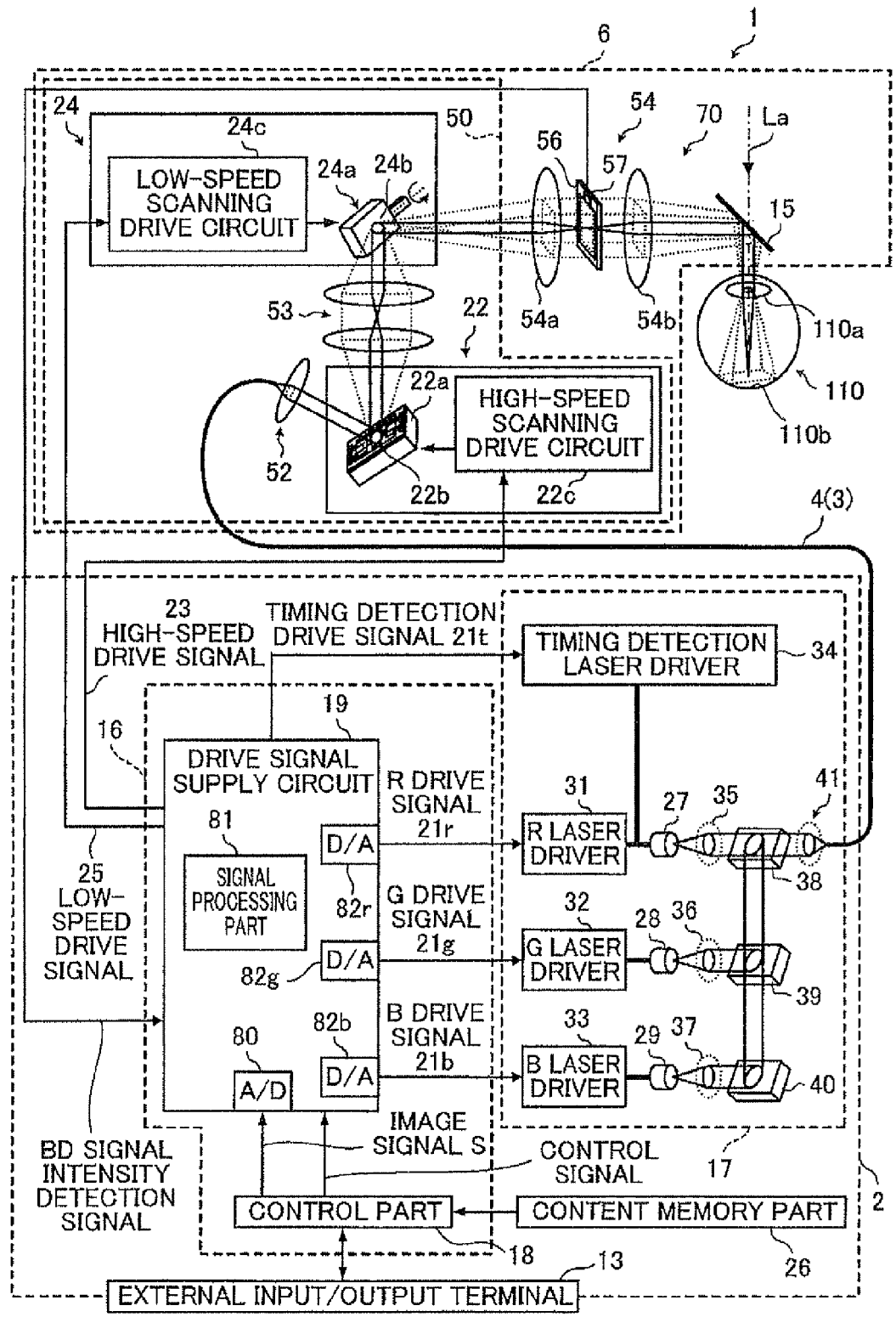
FIG. 4 is a block diagram showing the electric constitution of the vicinity of a control part.

Firstly, the schematic constitution of the RSD 1 according to this embodiment is explained in conjunction with FIG. 1 and FIG. 4.

As shown in FIG. 1, the RSD 1 according to this embodiment includes a drive control part 16, a light source part 17, a scanning part 50, and a projection part 70.

The drive control part 16, in response to an operation of an operation part (not shown in the drawing) or the like, generates a drive signal including an image signal corresponding to image information F, and outputs the drive signal to the light source part 17. The drive control part 16 also generates a drive signal for driving the scanning part 50 so that the scanning part 50 is operated.

The light source part 17 radiates a laser beam having intensity corresponding to the drive signal outputted from the drive control part 16. The laser beam radiated from the light source part 17 is scanned by the scanning part 50 in two-dimensional directions, and the scanned laser beam is projected onto a retina 110b of an eye 110 of a user who is a viewer by the projection part 70. Due to such a constitution, the laser beam whose intensity is modulated corresponding to the image information F (hereinafter referred to as "laser beam for forming an image") is scanned in two-dimensional directions on the retina 110b of the eye of the user thus allowing the user to visually recognize an image corresponding to the image information F.

Further, in the RSD 1, a light detection part 57 is arranged in an ineffective scanning range on a scanning trajectory of the laser beam by the scanning part 50. The light detection part 57 obtains a scanning position where the scanning part 50 scans by detecting scanning timing at which the laser beam is scanned thus adjusting radiation timing of the laser beam radiated from the light source part 17.

To be more specific, as shown in FIG. 1 and FIG. 4, in the scanning part 50, a deflecting surface 22b of a deflecting element 22a is swung in response to a high-speed drive signal 23 which is inputted to a high-speed scanning drive circuit 22c described later from the drive control part 16, and a deflecting surface 24b of a deflecting element 24a is swung in response to a low-speed drive signal 25 which is inputted to a low-speed scanning drive circuit 24c from the drive control part 16 thus scanning the image light two-dimensionally.

However, the swinging of the deflecting surfaces 22b, 24b does not completely agree with signal waveforms of the drive signals 23, 25 thus generating the phase difference or the like. Particularly, it is necessary for the deflecting element 22a to swing the deflecting surface 22b at a high speed, and the deflecting element 22a is a resonance-type deflecting element and hence, the phase difference between the swinging of the deflecting surface 22b and the signal waveform of the high-speed drive signal 23 becomes large.

Accordingly, in the RSD 1 according to this embodiment, to detect the scanning timing of a laser beam from the deflecting surface 22b, 24b, a laser beam for timing detection radiated from the light source part 17 is detected by the light detection part 57 thus adjusting the radiation timing of the laser beam for forming an image from the light source part 17. In the explanation made hereinafter, a point of time that the scanning timing is detected is also referred to as "timing detection time".

That is, the drive control part 16 controls the light source part 17 such that the light source part 17 radiates a laser beam having predetermined intensity (hereinafter referred to as "laser beam for timing detection") when the scanning position of the scanning part 50 falls within an ineffective scanning range which is a range other than an effective scanning range Z where the laser beam for forming an image is scanned. The drive control part 16, when the light detection part 57 detects the laser beam for timing detection, detects the scanning position of the scanning part 50 based on a detection signal outputted from the light detection part 57. Then, when the scanning position of the scanning part 50 falls within a predetermined effective scanning range, the drive control part 16 controls the light source part 17 such that the light source part 17 radiates the laser beam for forming an image. Accordingly, the laser beam for forming an image is scanned with high accuracy within the effective scanning range thus enhancing quality of an image visually recognized by a user. Between the scanning part 20 and the projection part 70, there is provided a light blocking part 56 which blocks the laser beam for timing detection which is scanned in the ineffective scanning range and advances toward an eye of the user.

Here, the intensity of the laser beam incident on the eye 110 of the user is extremely weak so that it is necessary to provide a light detection part having high sensitivity to detect such a laser beam. However, the manufacture and the development of the light detection part having high sensitivity are difficult and costly so that when such a light detection part of high sensitivity is adopted, this pushes up a manufacturing cost of the RSD.

Figure 2:
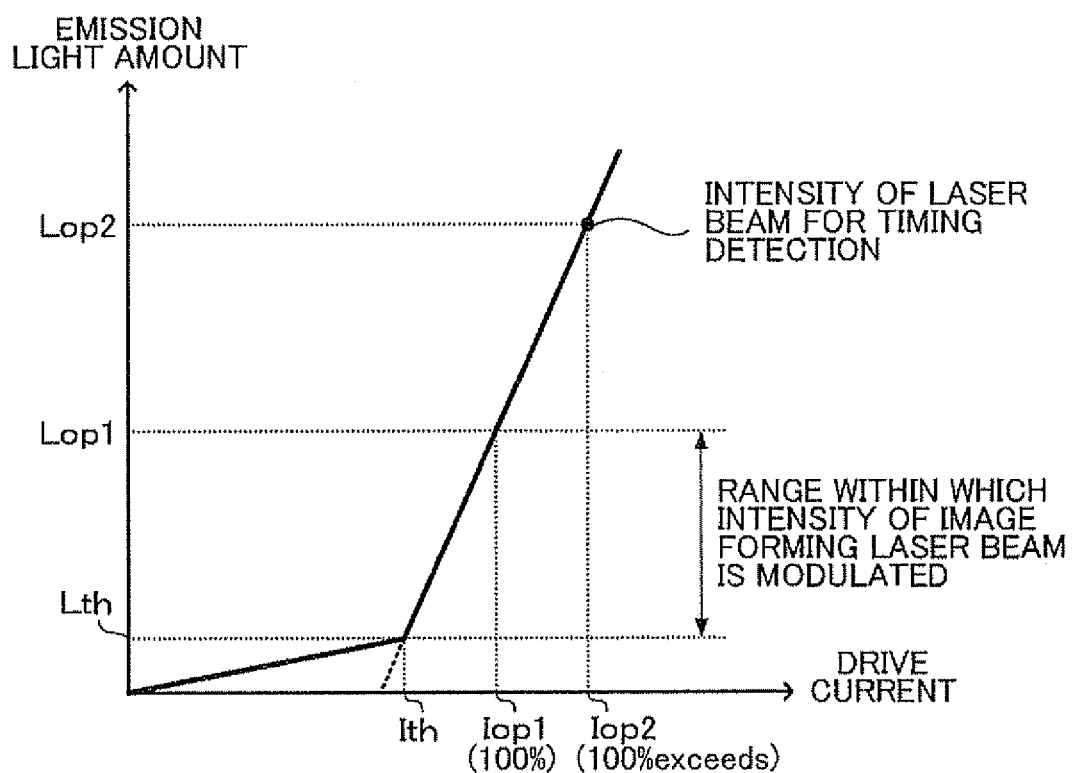
FIG. 2 is an explanatory view showing the electrical constitution and optical constitution of the retinal scanning display according to the embodiment.

Accordingly, as shown in FIG. 2, the drive control part 16 of the RSD 1 according to this embodiment is configured to radiate the laser beam for timing detection from the light source part 17 with intensity which exceeds a maximum value of intensity of the laser beam radiated from the light source part 17 at the image forming time. By increasing the intensity of the laser beam for timing detection, it is possible to suppress sensitivity of the light detection part by an amount corresponding to the increase of the intensity of the laser beam for timing detection thus suppressing the elevation of the cost.

It is desirable to set the intensity of the laser beam for timing detection to intensity necessary for outputting a detection signal in a preset optimum state from the light detection part 57. However, the intensity of the laser beam for timing detection is set to intensity equal to or lower than a safety value which ensures safety with respect to eyes of a user who is a viewer.

[2. Specific Constitution of RSD]

The constitution and the manner of operation of the RSD 1 which have been explained heretofore are further specifically explained in conjunction with drawings.

(Appearance of RSD)

Figure 3:
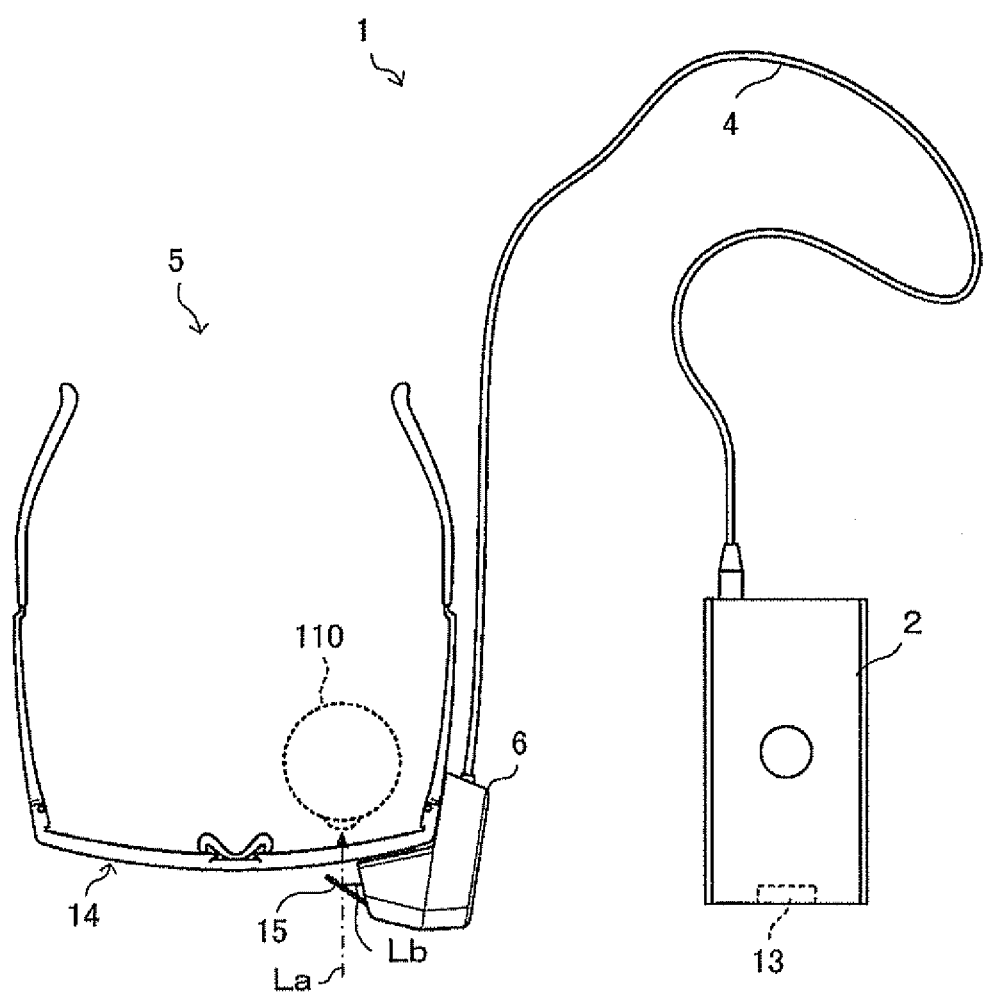
FIG. 3 is an explanatory view showing the constitution of the retinal scanning display according to the embodiment.

As shown in FIG. 3, the RSD 1 according to this embodiment includes a control unit 2, a head mounting device 5, and a cable 4 which connects the control unit 2 and the head mounting device 5.

As shown in FIG. 3 and FIG. 4, the control unit 2 forms an image signal based on content information stored in a content memory part 26 (described later) incorporated in the control unit 2, and radiates laser beams (hereinafter also referred to as "image lights") whose intensities are modulated for respective colors (R, G, B) corresponding to the image signal to the cable 4.

Further, the control unit 2 has an external input/output terminal 13, and receives inputting of an image signal from the outside, and can perform transmission and reception of content information or the like for forming an image signal between the control unit 2 and a personal computer or the like not shown in the drawing. Here, content information is constituted of at least one data out of data for displaying characters, data for displaying an image, and data for displaying an animated picture. For example, content information is a document file, an image file, an animated picture file or the like which is used in a personal computer or the like.

The cable 4 includes an optical fiber cable 3 described later which transmits the image light radiated from the control unit 2. The cable 4 also includes a drive signal transmission cable for transmitting a high-speed drive signal 23 and a low-speed drive signal 25 for synchronizing respectively a high-speed scanning part 22 and a low-speed scanning part 24 which are provided to the projection unit 6 described later with the light source part 17 described later.

The head mounting device 5 is configured, when a user mounts the head mounting device 5 on his head, to scan the transmitted image light, to project the scanned image light onto an eye of the user, and to display an image to the user. The head mounting device 5 is constituted of the projection unit 6 and an eyeglasses-type frame 14 which supports the projection unit 6. The projection unit 6 scans the image light which is transmitted through the optical fiber cable 3 of the cable 4, and projects the scanned image light onto an eye of the user who mounts the head mounting device 5 on his head and is a viewer thus displaying an image to the user.

The projection unit 6 allows the image light which is scanned in the two-dimensional directions to be incident on an eye 110 of the user, and scans the image light in the two-dimensional directions on a retina of the eye 110 of the user who is a viewer. Due to such a constitution, the user can visually recognize an image corresponding to the image information.

The projection unit 6 is provided with a half mirror 15 at a position where the half mirror 15 faces the eye 110 of the user who is a viewer. Due to such a constitution, an external light La passes through the half mirror 15 and is incident on the eye 110 of the user, and the image light Lb radiated from the projection unit 6 is reflected on the half mirror 15 and is incident on the eye 110 of the user. Accordingly, the user can visually recognize an image which is formed by superposing the image generated by the image light to scenery generated by the external light La.

In this manner, the RSD 1 is a see-through-type head mounted display which projects the image light onto the eye 110 of the user who is a viewer while allowing the external light to pass therethrough and to be incident on the eye 110 of the user.

[Specific Electrical Constitution and Specific Optical Constitution of RSD]

Next, the electrical constitution and the optical constitution of the RSD 1 are explained in conjunction with FIG. 4.

As shown in FIG. 3 and FIG. 4, the RSD 1 includes the control unit 2, the cable 4 (optical fiber cable 3), and the projection unit 6. The control unit 2 includes the drive control part 16 which performs a systematic control of the operation of the whole RSD 1, and a light source part 17 which generates image lights which are laser beams whose intensities are modulated for respective colors of R (red), G (green) and B (blue) in response to drive signals supplied from the drive control part 16, and radiates the generated image lights, (Drive Control Part 16)

The drive control part 16 includes a control part 18 which generates an image signal S based on image data, and a drive signal supply circuit 19 which generates drive signals for driving the light source part 17 in response to the image signal S generated by the control part 18.

The control part 18 reads content information which is preliminarily stored in a content memory part 26 having a memory area of a relatively large capacity, converts image data based on the content information into an image signal S, and supplies the image signal S to the drive signal supply circuit 19. Further, the control part 18 can also convert image data supplied from an external device not shown in the drawing which is connected to the control part 18 through an external input/output terminal 13 into an image signal S, and can supply the image signal S to the drive signal supply circuit 19. Here, the content memory part 26 may be formed of a magnetic memory medium such as a hard disk, an optical memory medium such as a CD-R, a non-volatile memory such as a flash memory or the like, for example.

Based on the image signal S supplied from the control part 18, the drive signal supply circuit 19 generates signals which respectively constitute elements for forming a display image. That is, based on the image signal S, the drive signal supply circuit 19 generates an R (red) drive signal 21*r*, a G (green) drive signal 21*g*, and a B (blue) drive signal 21*b*. The drive signal supply circuit 19 includes an A/D converter 80 which converts the image signal S into a digital signal, and a signal processing part 81 which, based on the image signal S which is digitally converted by the A/D converter 80, generates digital signals corresponding to brightness of R (red) component, brightness of G (green) component, and brightness of B (blue) component of each pixel of an image corresponding to the image signal S. The drive signal supply circuit 19 further includes D/A converters 82*r*, 82*g*, 82*b* which convert the digital signals corresponding to brightness of respective colors into drive signals 21*r*, 21*g*, 21*b*. That is, the D/A converter 82*r* converts the digital signal corresponding to brightness of the R component into the R (red) drive signal 21*r* which is an analogue signal. The D/A converter 82*g* converts the digital signal corresponding to brightness of the G component into the G (green) drive signal 21*g* which is an analogue signal. Further, the D/A converter 82*b* converts the digital signal corresponding to brightness of the B component into the B (blue) drive signal 21*b* which is an analogue signal. The digital signals corresponding to brightness of the respective colors are digital signals of 8 bits, for example, and the respective D/A converters 82*r*, 82*g*, 82*b* are D/A converters of 8 bits.

Further, the drive signal supply circuit 19 outputs a high-speed drive signal 23 which is used in the high-speed scanning part 22 described later and a low-speed drive signal 25 which is used in the low-speed scanning part 24.

Further, the drive signal supply circuit 19 outputs a timing detection drive signal 21*t* which allows the R laser beam source 27 to radiate a timing detection laser beam to the light source part 17. As described above, the timing detection drive signal 21*t* is provided for detection of the timing detection laser beam by the light detection part 57. The drive control part 16 detects a scanning position of the scanning part 50 at the detected timing of the timing detection laser beam by the light detection part 57, and adjusts the radiation timing of the laser beam from the light source part 17.

(Light Source Part 17)

The light source part 17 includes an R laser driver 31 for driving an R laser beam source 27, a G laser driver 32 for driving a G laser beam source 28, and a B laser driver 33 for driving a B laser beam source 29. The R laser driver 31 receives inputting of the R drive signal 21*r* outputted from the drive signal supply circuit 19, and outputs an amount of a drive current corresponding to the drive signal 21*r* to the R laser beam source 27. The G laser driver 32 receives inputting of the G drive signal 21*g* outputted from the drive signal supply circuit 19, and outputs an amount of drive current corresponding to the drive signal 21*g* to the G laser beam source 28. The B laser driver 33 receives inputting of the B drive signal 21*b* outputted from the drive signal supply circuit 19, and outputs an amount of drive current corresponding to the drive signal 21*b* to the B laser beam source 29. Due to such a constitution, the respective laser beam sources 27, 28, 29 radiate laser beams whose intensities are respectively modulated (hereinafter, also referred to as "optical flux") in response to the drive signals 21*r*, 21*g*, 21*b* which are generated based on the image signal S. The intensities of laser beams radiated from the respective laser beam sources 27, 28, 29 are changed in 256 stages based on the respective drive signals 21*r*, 21*g*, 21*b* outputted from the respective D/A converters 82*r*, 82*g*, 82*b*. Accordingly, the laser beams of respective colors are expressed in 256 grayscales.

Each laser beam source 27, 28, 29 may be constituted of a semiconductor laser or a solid-state laser having a harmonics generating mechanism, for example. Here, when the semiconductor laser is used as the laser beam source 27, 28, 29, the intensity of the laser beam may be modulated by directly modulating a drive current. On the other hand, when the solid-state laser is used as the laser beam source 27, 28, 29, it is necessary to modulate the intensity of the laser beam by providing an external modulator to each laser beam source 27, 28, 29.

Further, the light source part 17 is provided with a timing detection laser driver 34 which allows the R laser beam source 27 to output a timing detection laser beam in response to the timing detection drive signal 21*t* outputted from the drive signal supply circuit 19. The timing detection laser driver 34 is electrically connected to the R laser beam source 27.

The timing detection laser driver 34, upon receiving the timing detection drive signal 21*t*, outputs a drive current corresponding to the timing detection drive signal 21*t* to the R laser beam source 27. That is, the timing detection laser driver 34 functions as a second drive part which generates the timing detection drive signal 21*t* for radiating the laser beam from the light source part 17 at the timing detection time, and outputs the timing detection drive signal 21*t* to the light source part 17. Due to such a constitution, a timing detection laser beam having intensity corresponding to the timing detection drive signal 21*t* is radiated from the R laser beam source 27.

This timing detection laser beam is radiated with intensity which exceeds maximum values of intensities of laser beams which are radiated from the R laser beam source 27, the G laser beam source 28 and the B laser beam source 29 based on the R drive signal 21*r*, the G drive signal 21*g* and the B drive signal 21*b* generated based on the image signal S at the image forming time.

Accordingly, this embodiment can eliminate insufficient accuracy (for example, jitter in many cases) in timing detection based on the shortage of received light in the light detection part 57 described later so that a scanning position of the scanning part 50 can be accurately detected thus preventing the occurrence of disturbance of an image attributed to the insufficient accuracy in timing detection.

Here, in this embodiment, a drive current outputted from the R laser driver 31 and a drive current outputted from the timing detection laser driver 34 are respectively individually inputted to the R laser beam source 27. That is, the R laser driver 31 sets the output impedance thereof to high resistance when the R drive signal 21*r* is not inputted thereto, while the timing detection laser driver 34 sets the output impedance thereof to high resistance when the timing detection drive signal 21*t* is not inputted thereto. A drive current outputted from the R laser driver 31 and a drive current outputted from the timing detection laser driver 34 may be inputted to the R laser beam source 27 after being added to each other.

Further, the timing detection laser beam radiated from the R laser beam source 27 has intensity which is necessary for outputting a detection signal in a preliminarily regulated optimum state as a detection signal outputted from the light detection part 57 which detects the timing detection laser beam.

To be more specific, the timing detection laser beam is radiated from the light source part 17 with intensity which allows the timing accuracy of a BD signal 58 outputted from the light detection part 57 to fall within a predetermined proper range intrinsic to the device. In other words, the intensity of the laser beam radiated from the light source part 17 at the timing detection time is set to a proper level which is determined based on the specification of the light detection part 57. This proper level is a level defined as an incidence level which is intrinsic to an optical device such as a BD sensor, an optical sensor or the like and can detect the timing with sufficient accuracy. A rated level or the like may be one example of the proper level.

Due to such a constitution, it is possible to prevent the occurrence of a phenomenon that intensity of the timing detection light incident on the light detection part 57 is so weak that an S/N ratio of the BD signal 58 outputted from the light detection part 57 is deteriorated.

Further, the timing detection laser beam radiated from the R laser beam source 27 is radiated with intensity equal to or lower than a safety value of laser intensity which can ensure safety for an eye of a user who is a viewer.

This safety value may be, in general, a value recommended by ISO standard, JIS standard or the like or may be a newly stipulated value as a value which does not adversely influences an eye of a person even when a laser beam is incident on the eye. To give one example, the safety value may be not more than 390 µW which is a reference value (Class 1) which IEC (International Electrotechnical Commission) stipulates.

In the RSD 1 according to this embodiment, the R laser beam source 27 is used as the laser which radiates the timing detection laser beam. However, among the R laser beam source 27, the G laser beam source 28 and the B laser beam source 29, provided that the laser can radiate a laser beam of a wavelength which can be detected by the light detection part 57 with optimum sensitivity, the laser which radiates the timing detection laser beam is not limited to the R laser beam source 27. However, a photosensor which constitutes the light detection part 57 can detect a red-oriented laser beam with optimum sensitivity in general and hence, it is desirable to use R laser beam source 27 as the laser beam source which radiates the timing detection laser beam.

Further, the light source part 17 includes collimation optical systems 35, 36, 37 which are provided for collimating the laser beams radiated from the respective laser beam sources 27, 28, 29, dichroic mirrors 38, 39, 40 which synthesize the collimated laser beams, and a coupling optical system 41 which guides the synthesized laser beams to the optical fiber cable 3.

In this manner, the laser beams radiated from the respective laser beam sources 27, 28, 29 are collimated by the collimation optical systems 35, 36, 37 respectively and, thereafter, are incident on the dichroic mirrors 38, 39, 40 respectively. Then, the respective laser beams are reflected on or are allowed to pass through these dichroic mirrors 38, 39, 40 selectively corresponding to wavelengths thereof, arrive at the coupling optical system 41, and are converged by the coupling optical system 41. Then, the converged laser beams are outputted to the optical fiber cable 3.

(Projection Unit 6)

The projection unit 6 which is positioned between the control unit 2 and an eye 110 of a user who is a viewer includes the scanning part 50 and the projection part 70 (a second relay optical system 54, the light detection part 57, the light blocking part 56, and the half mirror 15). The scanning part 50 scans the laser beams which are generated by the light source part 17 and are radiated through the optical fiber cable 3 in the two-dimensional directions. Within the scanning range of the scanning part 50, the image forming laser beam which is scanned within the effective scanning range Z is incident on the retina 110*b* of the eye 110 of the viewer via the second relay optical system 54 and the half mirror 15. Here, the projection part 70 is constituted of a second lens 54*b* and the half mirror 15.

To be more specific, the scanning part 50 includes a collimation optical system 52 which collimates the laser beams radiated through the optical fiber cable 3, and a high-speed scanning part 22 which scans the laser beams collimated by the collimation optical system 52 in the horizontal direction (X direction in FIG. 1) which constitutes a first direction in a reciprocating manner for displaying an image. The scanning part 50 also includes a low-speed scanning part 24 which scans the laser beams scanned in the horizontal direction by the high-speed scanning part 22 in the vertical direction (Y direction in FIG. 1) which constitutes a second direction, and a first relay optical system 53 which is arranged between the high-speed scanning part 22 and the low-speed scanning part 24, and radiates the scanned laser beams to the projection part 70. In the RSD 1 of this embodiment, the scanning in the first direction by the high-speed scanning part 22 is set as the horizontal scanning and the scanning in the second direction by the low-speed scanning part 24 is set as the vertical scanning. However, the scanning directions are not limited to such setting, and the scanning in the first direction may be set as the vertical scanning and the scanning in the second direction may be set as the horizontal scanning depending on specification of a product or the like.

The high-speed scanning part 22 and the low-speed scanning part 24 are optical systems which, to bring the laser beams incident from the optical fiber cable 3 into a state which allows the laser beams to be projected onto the retina 110b of the viewer as an image, scan the laser beams in the horizontal direction as well as in the vertical direction so as to form the laser beams into scanned optical fluxes.

The high-speed scanning part 22 includes a resonance-type deflecting element 22a having a deflecting surface which functions as a first optical scanning element for scanning the laser beams in the horizontal direction, and a high-speed scanning drive circuit 22c which, based on the high-speed drive signal 23, generates a drive signal for resonating the deflecting element 22a so as to swing the deflecting surface 22b which functions as a reflection mirror.

On the other hand, the low-speed scanning part 24 includes a non-resonance-type deflecting element 24a having a deflecting surface which functions as a second optical scanning element for scanning the laser beams in the vertical direction, and a low-speed scanning drive circuit 24c which generates, based on a low-speed drive signal 25, a drive signal for forcibly swinging the deflecting surface 24b of the deflecting element 24a in a non-resonant state. Here, the low-speed scanning part 24 scans the laser beams which are scanned in the horizontal direction for forming the image in the vertical direction for every 1 frame of an image to be displayed thus forming a two-dimensionally scanned image.

Further, the first relay optical system 53 is arranged between the high-speed scanning part 22 and the low-speed scanning part 24, and relays the laser beams. The first relay optical system 53 converges the laser beams which are scanned in the horizontal direction by the deflecting surface 22b of the deflecting element 22a on the deflecting surface 24b of the deflecting element 24a. Further, the converged laser beams are scanned in the vertical direction by the deflecting surface 24b of the deflecting element 24a, and is radiated to the projection part 70 as the image light.

Figure 5:
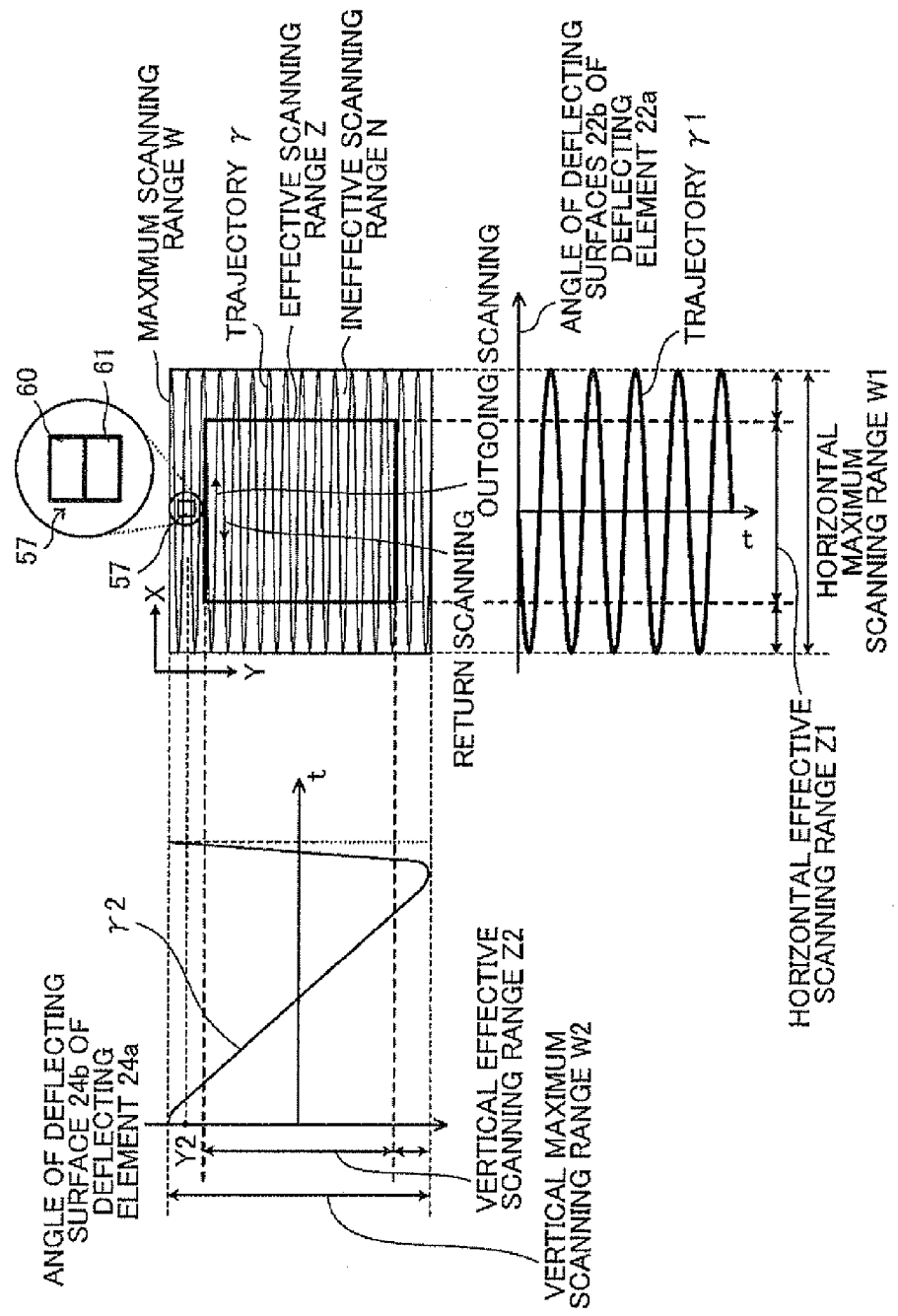
FIG. 5 is a flowchart showing the flow of processing executed by the retinal scanning display according to the embodiment.

That is as shown in FIG. 5, in the deflecting element 22a which swings at a relatively high speed, the deflecting surface 22b of the deflecting element 22a is swung in a sinusoidal manner by the high-speed scanning drive circuit 22c (swinging trajectory γ1) thus scanning an incident optical flux in a reciprocating manner with respect to the horizontal direction X. The laser beam scanned in the horizontal direction X by the deflecting element 22a is incident on the low-speed scanning part 24 via the first relay optical system 53. In the deflecting element 24a of the low-speed scanning part 24, the deflecting surface 24b of the deflecting element 24a is swung by the low-speed scanning drive circuit 24c in a saw-tooth manner (swinging trajectory γ2) thus scanning the incident laser beam with respect to the vertical direction Y. Then, the laser beam in an effective scanning range Z scanned in the vertical direction Y by the deflecting element 24a is incident on a pupil 110a of a viewer via the projection part 70.

FIG. 5 shows the relationship between a maximum scanning range W (a range formed by a horizontal maximum scanning range W1 and a vertical maximum scanning range W2) of the deflecting element 22a and the deflecting element 24a and an effective scanning range Z (a range formed by a horizontal effective scanning range Z1 and a vertical effective scanning range Z2). Here, the "maximum scanning range" implies a maximum range where light can be scanned by the deflecting element 22a and the deflecting element 24a.

By radiating the image forming laser beam whose intensity is modulated in response to an image signal S from the light source part 17 at timing where the scanning positions of the deflecting element 22a and the deflecting element 24a are arranged in the effective scanning range Z within the maximum scanning range W, the image forming laser beam is scanned within the effective scanning range Z by the high-speed scanning part 22 and the low-speed scanning part 24.

Accordingly, the image forming laser beam for 1 frame is scanned. This scanning is repeated for every image of 1 frame. In FIG. 5, a trajectory γ of the laser beam scanned by the high-speed scanning part 22 and the low-speed scanning part 24 assuming that the laser beam is constantly radiated from the light source part 17 is virtually shown. Further, in the explanation made hereinafter, a range N which is formed by removing the effective scanning range Z from the scanning range W is referred to as "ineffective scanning range N".

Returning to the explanation in conjunction with FIG. 4, in the second relay optical system 54, a first lens 54a, a second lens 54b each of which has a positive refractive power are arranged in series. The second relay optical system 54 converges the laser beams for forming the image which are scanned by the scanning part 50 using the first lens 54a and the second lens 54b, and the converged laser beams are incident on the pupil 110a of the eye 110 of a viewer via the half mirror 15.

Here, the drive control part 16 sequentially supplies the drive signals corresponding to the image signal S to the respective laser beam sources 27, 28, 29 of the light source part 17 when the scanning position of the scanning part 50 is in the effective scanning range Z thus allowing the respective laser beam sources 27, 28, 29 to sequentially radiate the image forming laser beams.

Accordingly, the image forming laser beam is incident on the scanning part 50 via the respective dichroic mirrors 38, 39, 40, the coupling optical system 41 and the optical fiber cable 3, and the image forming laser beam is scanned two-dimensionally in the effective scanning range Z by the scanning part 50. Then, the image forming laser beam scanned two-dimensionally by the scanning part 50 is incident on the pupil 110a of the eye 110 of the viewer via the projection part 70 so that the image fanning laser beam is projected on the retina 110b. Due to such an operation, the viewer can recognize an image formed by the image forming laser beam projected on the retina 110b. In this manner, the projection part 70 projects the laser beam which is radiated from the light source part 17 at the image forming time and is scanned by the scanning part 50 on the retina 110b of the eye 110 of the viewer thus projecting an image on the retina 110.

Further, the laser beam scanned by the scanning part 50 forms an intermediate image plane which has the image conjugate relationship with the retina 110b of the eye 110 of the viewer between the first lens 54a and the second lens 54b of the second relay optical system 54.

Further, in the RSD 1 according to this embodiment, in the vicinity of a position where the intermediate image plane of the second relay optical system 54 of the projection part 70 is arranged, the light blocking part 56 is arranged. This light blocking part 56 is provided as a light blocking part which blocks light scanned in the ineffective scanning range N and allows the light scanned in the effective scanning range Z to pass therethrough with respect to the light scanned in the maximum scanning range W. In the light blocking part 56, a light detection part 57 which detects the detection timing laser beam scanned in the ineffective scanning range N and the intensity adjustment laser beam is formed.

The light blocking part 56 is arranged between the scanning part 50 and the viewer, and plays a role of blocking the laser beam which is scanned by the scanning part 50 and advances toward the eye 110 of the viewer at the timing detection time.

Figure 6:
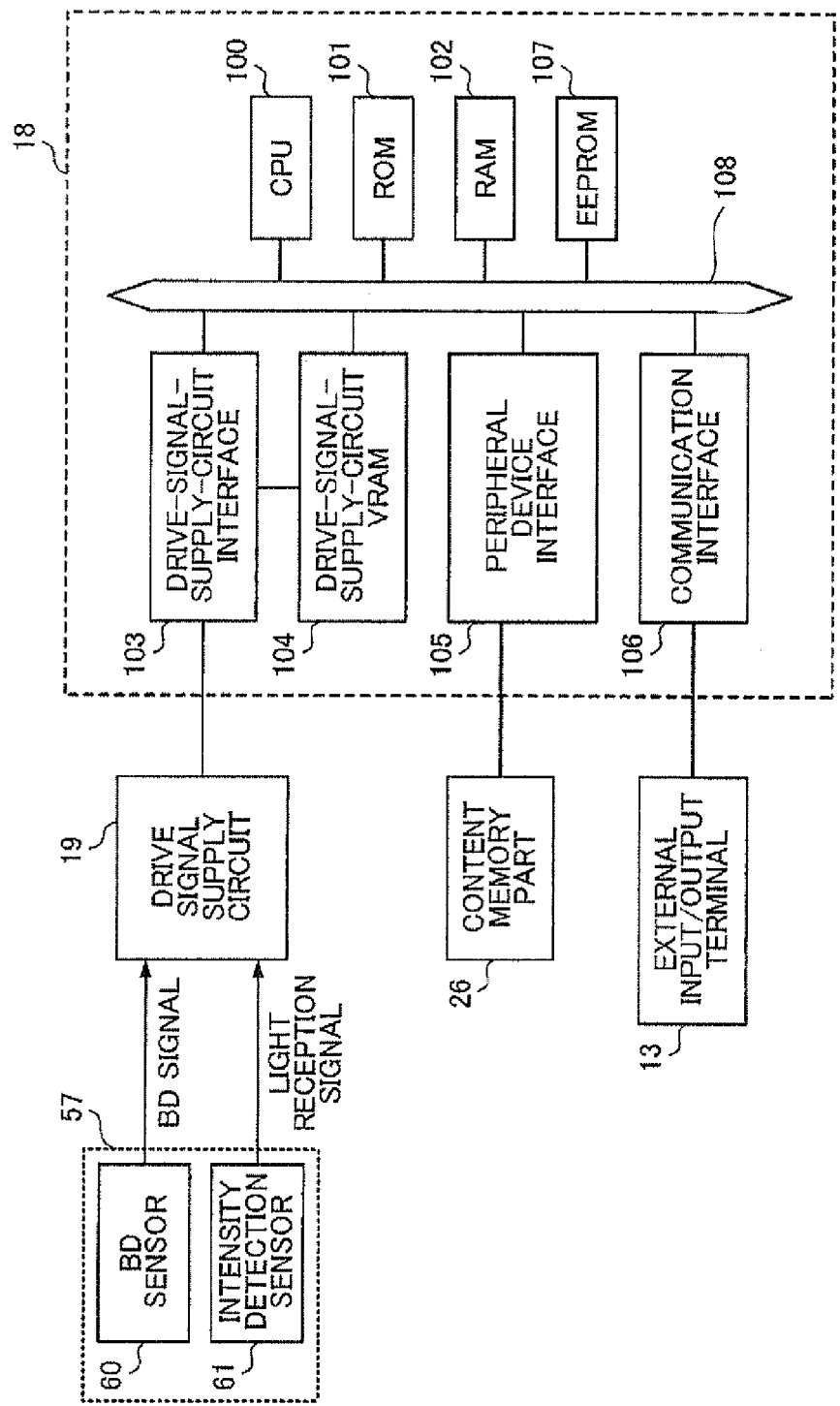
FIG. 6 is a flowchart showing the flow of processing executed by the retinal scanning display according to the embodiment.

Further, the light detection part 57 is arranged at a position where the laser beam which is radiated from the light source part 17 at the time of detecting timing of the scanning part 50 and is scanned by the scanning part 50 is incident. As shown in FIG. 5 and FIG. 6, the light detection part 57 includes a BD sensor 60 and an intensity detection sensor 61. When the timing detection laser beam is incident on the BD sensor 60, the BD sensor 60 outputs a BD signal 58 to the control part 18. On the other hand, the intensity detection sensor 61, when the intensity adjustment laser beam is incident on the intensity detection sensor 61, outputs a light reception signal corresponding to the intensity of the intensity adjustment laser beam to the control part 18. The BD sensor 60 outputs the steep rising BD signal 58 when the BD sensor 60 detects the laser beam. For example, the BD sensor 60 may be formed by arranging two photo diodes (hereinafter referred to as "PD") parallel to each other in the X direction. Here, an electric current which flows in one PD is converted into a first voltage, an electric current which flows in the other PD is converted into a second voltage, and the BD signal 58 is generated by comparing the first voltage and the second voltage which are shifted from each other by a comparator. On the other hand, the intensity detection sensor 61 generates a voltage corresponding to intensity of the detected laser beam, and outputs the voltage as a reception signal. The intensity detection sensor 61 is, for example, constituted of one photo diode and a current/voltage conversion circuit.

The control part 18 which receives the BD signal 58 from the BD sensor 60 adjusts timing of laser beam radiated from the light source part 17 based on the BD signal 58. Further, the control part 18 which receives the light reception signal from the intensity detection sensor 61 adjusts the intensity of the image forming laser beam.

[Electrical Constitution of Control Part 18]

Next, the constitution of the control part 18 arranged in the inside of the drive control part 16 is explained in conjunction with FIG. 6.

The control part 18 includes a CPU 100, a ROM 101, a RAM 102, an EEPROM 107, a drive-signal-supply-circuit interface 103, a drive-signal-supply-circuit VRAM 104, a peripheral device interface 105 and a communication interface 106. These constitutional elements are connected with each other via a system bus 108.

In the ROM 101, a program which realizes processing in accordance with a flow chart described later when executed by the CPU 100 and a current value necessary for radiating the laser beam for timing detection are stored. The RAM 102 functions as a temporary storage region which stores various variables which are looked up when the CPU 100 executes the program stored in the ROM 101. The EEPROM 107 functions as a storage region which stores variables or the like to be held even after the supply of electricity to the RSD 1 is stopped.

For example, in the EEPROM 107, a value which indicates a shift rate between a timing adjustment mode and an intensity adjustment mode and the like are stored.

The drive-signal-supply-circuit interface 103 is provided for connecting the control part 18 and the drive signal supply circuit 19, and generates an image signal S by looking up the drive-signal-supply-circuit VRAM 104, and supplies the image signal S to the drive signal supply circuit 19. With respect to the drive-signal-supply-circuit VRAM 104, as described previously, the drive-signal-supply-circuit interface 103 supplies the image signal S to the drive signal supply circuit 19 by looking up this drive-signal-supply-circuit VRAM 104. The peripheral device interface 105 is provided for an operational control of peripheral devices connected to the control part 18 and the transmission and reception of the signals with these peripheral devices. To this peripheral device interface 105, a content storage part 26, and a power source button, an operation button and the like not shown in the drawing are connected. The communication interface 106 is provided for transmission and reception of signals with devices connected to the control part 18, and is connected with an external input/output terminal 13 and the light detection part 57.

[Processing Operation of Control Part 18]

Next, processing executed by the drive control part 16 in the RSD 1 is explained in conjunction with FIG. 7A to FIG. 9.

Figure 7A:
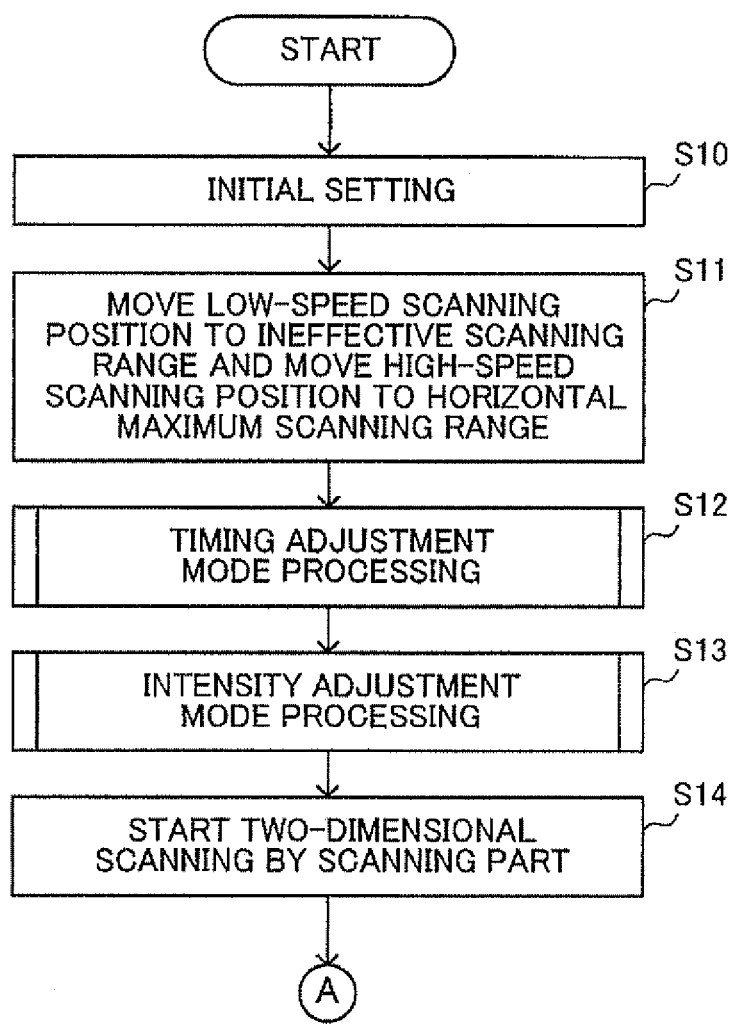
FIGS. 7A and 7B are flowcharts showing the flow of processing executed by the retinal scanning display according to the embodiment.

Firstly, to explain the processing sequentially from main processing shown in FIG. 7A, the CPU 100 of the control part 18 executes initial setting such as the permission of access to the RAM 102 and the initialization of a working area (step S10).

Next, the CPU 100, when a laser beam is radiated from the light source part 17, controls the drive signal supply circuit 19 such that the laser beam passes the light detection part 57 at predetermined intervals, and a predetermined high-speed drive signal 23 and a predetermined low-speed drive signal 25 are outputted from the drive signal supply circuit 19. The high speed scanning drive circuit 22c drives the deflecting element 22a based on the inputted high-speed drive signal 23 so as to swing the deflecting surface 22b such that the scanning position moves within the horizontal scanning maximum range W1 (see γ1 in FIG. 5). Further, the low-speed scanning part 24 drives the deflecting element 24a based on the inputted low-speed drive signal 25 so as to move the deflecting surface 24b such that the scanning position passes a position in the ineffective scanning range and in the same vertical scanning direction Y as the light detection part 57 (position Y2 in FIG. 5) (step S11).

Next, the CPU 100 allows the drive signal supply circuit 19 to execute the timing adjustment mode processing in which the radiation timing of the image forming laser beam is adjusted (step S12). In this step, the deflecting surface 24b is held stationary and hence, in this timing adjustment mode processing, the timing of deflecting surface 22b is adjusted by the drive signal supply circuit 19 such that the phase difference between a signal waveform of the high-speed drive signal 23 and the deflecting surface 22b falls within a fixed range. That is, the drive signal supply circuit 19 detects the phase difference between the signal waveform of the high-speed drive signal 23 and the scanning position of the deflecting surface 22b. Further, the deflecting surface 24b is swung such that the scanning position passes the light detection part 57 within the ineffective scanning range N, and the phase difference between a signal waveform of the low-speed drive signal 25 and a swing surface of the deflecting surface 24b is detected by the drive signal supply circuit 19. Then, the drive signal supply circuit 19 calculates the scanning position of the deflecting surface 22b with respect to the high speed drive signal 23 and the scanning position of the deflecting surface 24b with respect to the high-speed drive signal 23 as information on the scanning position corresponding to the detected phase differences, and calculates the timing at which the image forming laser beam is radiated based on the information on the scanning position. This timing adjustment mode processing is explained in detail later in conjunction with FIG. 8.

Next, the CPU 100 controls the drive signal supply circuit 19 such that the drive signal supply circuit 19 executes the intensity adjustment mode processing in which the intensity of image forming laser beam is adjusted (step S13). This intensity adjustment mode processing is explained in detail later in conjunction with FIG. 9.

Next, the CPU 100 controls the drive signal supply circuit 19 such that when the laser beam is radiated from the light source part 17, the laser beam is scanned two-dimensionally by the scanning part 50. Accordingly, a predetermined high-speed drive signal 23 and a predetermined low-speed drive signal 25 are outputted from the drive signal supply circuit 19 (step S14). The high-speed scanning drive circuit 22e drives the deflecting element 22a based on the inputted high-speed drive signal 23, and moves the deflecting surface 22b such that the scanning position is changed within the horizontal scanning maximum range W1 (see γ1 in FIG. 5). Further, the low-speed scanning part 24 drives the deflecting element 24a based on the inputted low-speed drive signal 25, and swings the deflecting surface 24b such that the scanning position moves in the vertical scanning maximum range W2.

Thereafter, the CPU 100 reads image information F from the content storage part 26, converts the image information F into an image signal S, and inputs the image signal S to the drive signal supply circuit 19. The drive signal supply circuit 19 performs the image display processing and the adjustment of radiation timing and intensity of the laser beam by executing processing in succeeding steps S15 to S17, S12', S13'.

Figure 7B:
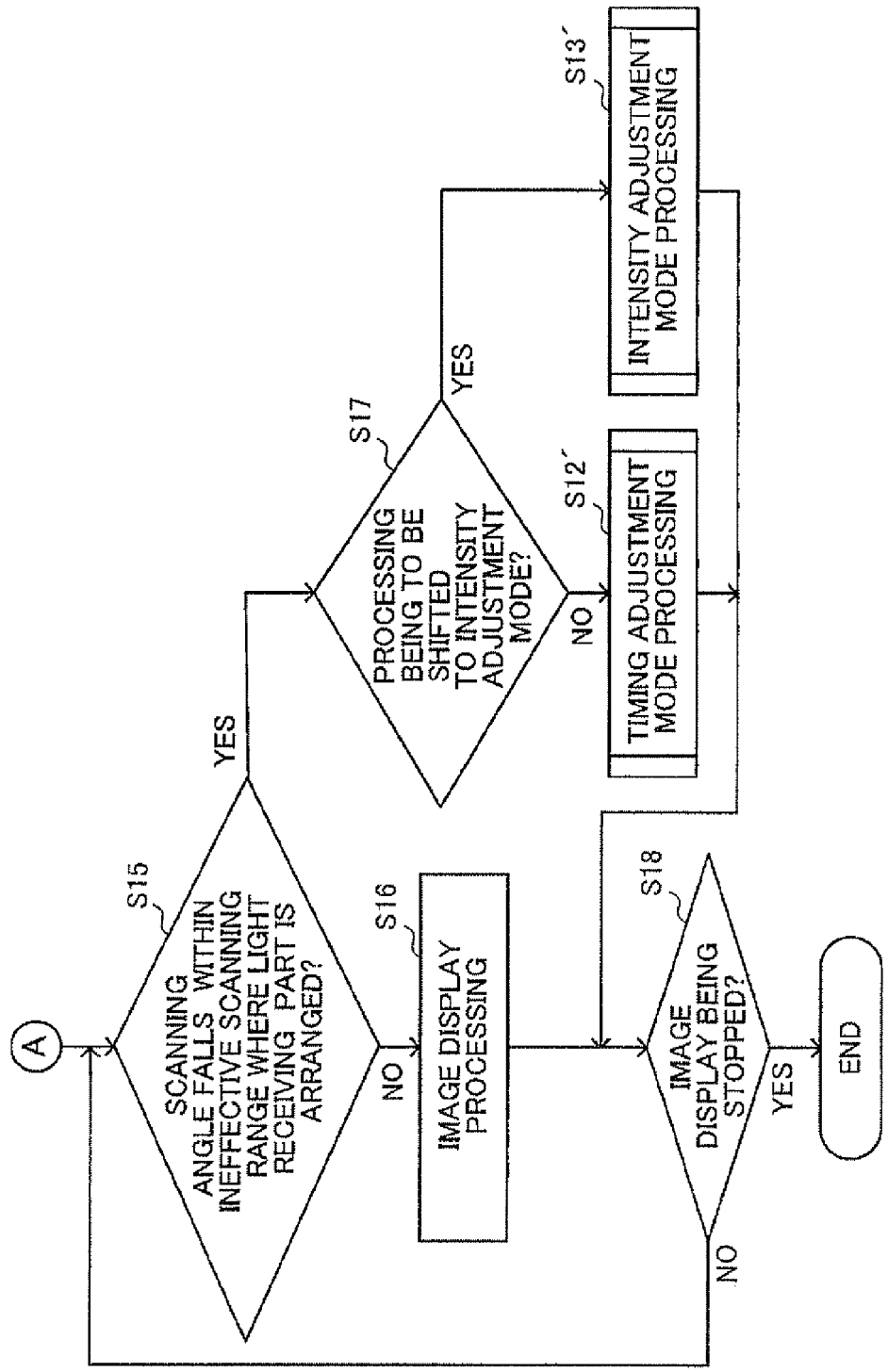

Firstly, as shown in FIG. 7B, the drive signal supply circuit 19 determines whether or not the scanning position (angle) of the deflecting surface 24b falls within an ineffective scanning range N where the light detection part 57 is arranged (step S15). In this processing, when the drive signal supply circuit 19 determines that the scanning position of the deflecting surface 24b does not fall within the ineffective scanning range N where the light detection part 57 is arranged (step S15: No), the drive signal supply circuit 19 executes image display processing in which an image forming laser beam is projected on a pupil 110a of a viewer (step S16). In this image display processing, the drive signal supply circuit 19 outputs drive signals 21r, 21g, 21b corresponding to the image signal S when the scanning position of the scanning part 50 falls within the effective scanning range Z. Accordingly, when the scanning position of the scanning part 50 falls within the effective scanning range Z, the image forming laser beam is radiated from the light source part 17, the image forming laser beam is scanned by the scanning part 50, and the image forming laser beam is projected on the pupil 110a of the viewer. The drive signal supply circuit 19 allows the light source part 17 to radiate the image forming laser beam when the deflecting surface 24b falls within the vertical effective scanning range Z2 and the scanning position of the deflecting surface 22b falls within the horizontal effective scanning range Z1, and allows the light source part 17 to stop the radiation of image forming laser beam from the light source part 17 when the scanning position of the deflecting surface 22b falls outside the horizontal effective scanning range Z1. In the execution of the processing of this step S16 by the CPU 100, the drive control part 16 functions as a first drive part which generates the image signal for radiating the laser beam from the light source part at the image forming time and outputs the image signal to the light source part.

On the other hand, when the drive signal supply circuit 19 determines that the scanning position of the deflecting surface 24b falls within the ineffective scanning range N where the light detection part 57 is arranged in the above-mentioned step S15 (step S15: Yes), the drive signal supply circuit 19 advances the processing to step S17.

In step S17, the drive signal supply circuit 19 determines whether or not the processing is to be shifted to the intensity adjustment mode by looking up a value which indicates a shift rate between a predetermined timing adjustment mode and the predetermined intensity adjustment mode. Although the shift rate is a value which the control part 18 allows the drive signal supply circuit 19 to set in response to inputting instructions to an operation part not shown in the drawing by a viewer, the shift rate may be set to a fixed value.

Here, when the drive signal supply circuit 19 determines that the processing is not to be shifted to the intensity adjustment mode (step S17: No), the drive signal supply circuit 19 advances the processing to step S12'.

In step S12', the drive signal supply circuit 19 executes the timing adjustment mode processing in which the adjustment of radiation timing of the image forming laser beam is performed in the same manner as processing in step S12. On the other hand, when the drive signal supply circuit 19 determines that the processing is to be shifted to the intensity adjustment mode in the above-mentioned step S17 (step S17: Yes), the drive signal supply circuit 19 advances the processing to step S13'.

In step S13', the drive signal supply circuit 19 executes the intensity adjustment mode processing where the intensity of the image forming laser beam is adjusted in the same manner as processing in step S13.

When the processings in steps S12' and S13' are finished, the drive signal supply circuit 19 determines whether or not the image display is stopped. That is, the drive signal supply circuit 19 determines whether or not the inputting of the image signal S from the control part 18 is stopped (step S18).

Here, when the drive signal supply circuit 19 determines that the image display is stopped (step S18: Yes), the drive signal supply circuit 19 finishes the image display processing. On the other hand, when the drive signal supply circuit 19 determines that the image display is not stopped (step S18: No), the CPU 100 returns the processing to step S15.

Here, with respect to the above-mentioned timing adjustment mode and intensity adjustment mode, it is desirable that the timing adjustment mode is executed for every frame, and the intensity adjustment mode is executed periodically at timing where the intensity adjustment mode does not occur simultaneously with the timing adjustment mode.

Figure 8:
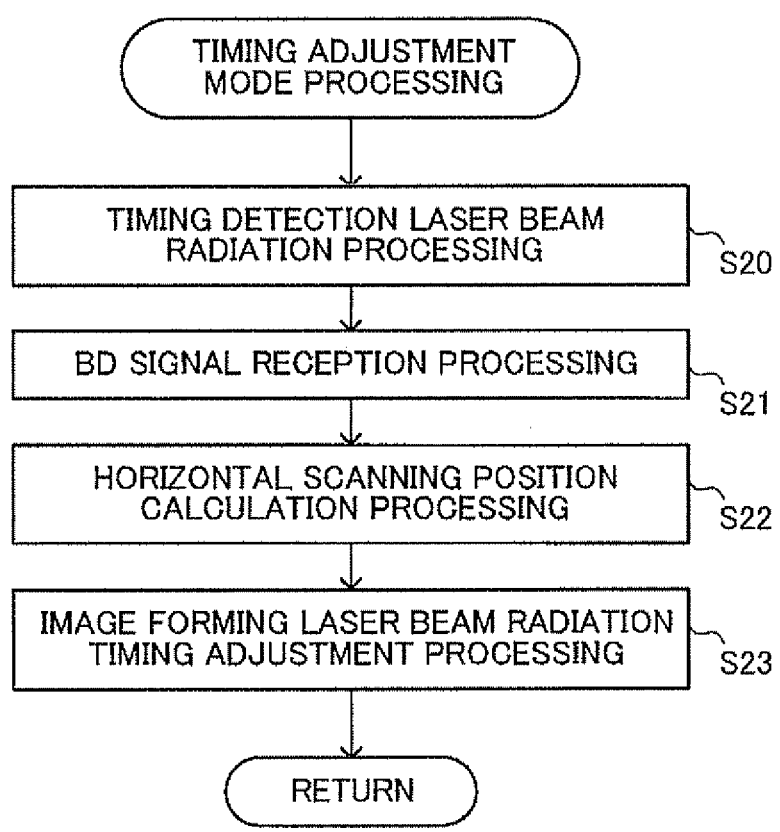
FIG. 8 is a flowchart showing the flow of processing executed by the retinal scanning display according to the embodiment.

Next, the timing adjustment mode processing described in steps S12, S12' of the main flow is explained in conjunction with FIG. 8.

In the timing adjustment mode processing, the drive signal supply circuit 19 firstly executes timing detection laser beam radiation processing (step S20).

To be more specific, the drive signal supply circuit 19 supplies a timing detection drive signal 21t to the timing detection laser driver 34. Here, the drive signal supply circuit 19 sets the intensity of the timing detection laser beam which is radiated from the R laser beam source 27 such that the intensity of the timing detection laser beam satisfies at least the following three conditions (i) to (iii) described previously.

(i) The intensity of the timing detection laser beam which is radiated from the R laser beam source 27 exceeds the maximum value of the intensity of the image forming laser beam.

(ii) The intensity of the timing detection laser beam which is radiated from the R laser beam source 27 is intensity where the S/N ratio of the BD signal 58 outputted from the BD sensor 60 becomes a predetermined optimum value.

(iii) The intensity of the timing detection laser beam which is radiated from the R laser beam source 27 is not more than a safety value for ensuring safety of an eye of a viewer.

In the execution of the processing of this step S20 by the CPU 100, the drive control part 16 functions as a second drive part which generates the timing detection drive signal for radiating the laser beam from the light source part at the timing detection time and outputs the timing detection drive signal to the light source part.

Next, the drive signal supply circuit 19 executes the BD signal reception processing where the drive signal supply circuit 19 receives a BD signal 58 outputted from the BD sensor 60 upon receiving the timing detection laser beam (step S21). Thereafter, the drive signal supply circuit 19 executes the calculation processing of the scanning position based on the BD signal 58 received in step S21 (step S22). For example, the drive signal supply circuit 19 detects the phase difference between a signal waveform of the outputted high-speed drive signal 23 and a swing waveform of the deflecting surface 22b, and the phase difference between a signal waveform of the outputted low-speed drive signal 25 and a swing waveform of the deflecting surface 24b. Then, the drive signal supply circuit 19 calculates the scanning position of the deflecting surface 22b with respect to the high speed drive signal 23 and the scanning position of the deflecting surface 24b with respect to the low-speed drive signal 25 as information on the scanning position corresponding to the detected phase differences.

Then, the drive signal supply circuit 19 executes the radiation timing adjustment processing of the image forming laser beam in which the timing at which the image forming laser beam is radiated is calculated based on the information on the scanning positions obtained in step S22 (step S23), and drive signal supply circuit 19 returns the processing to the main processing.

Figure 9:
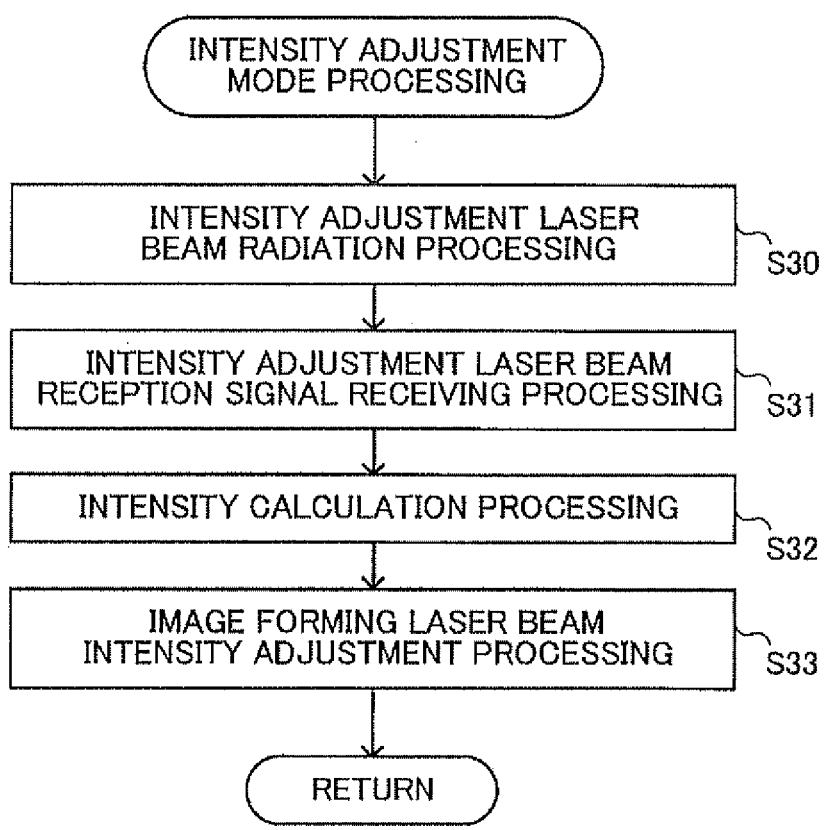
FIG. 9 is a flowchart showing the flow of processing executed by the retinal scanning display according to the embodiment.

Next, the intensity adjustment mode processing described in steps S13, S13' of the main flow is explained in conjunction with FIG. 9.

In the intensity adjustment mode processing, the drive signal supply circuit 19 firstly executes the intensity adjusting laser beam radiation processing (step S30).

To be more specific, the drive signal supply circuit 19 supplies respective drive signals 21r, 21g, 21b corresponding to the radiation of an image forming laser beam with maximum intensity to the respective laser drivers 31, 32, 33.

Here, with respect to the respective drive signals 21r, 21g, 21b which are supplied to the respective laser drivers 31, 32, 33 from the drive signal supply circuit 19, any one kind of drive signals may be outputted for every frame, or plural kinds of drive signals (for example, three kinds of drive signals 21r, 21g, 21b) may be outputted within a single frame.

Next, the drive signal supply circuit 19 executes the reception signal receiving processing where an intensity adjustment laser beam is received by the intensity detection sensor 61, and a light reception signal outputted from the intensity detection sensor 61 is received by the drive signal supply circuit 19 (step S31).

Next, the drive signal supply circuit 19 executes the intensity calculation processing based on the reception signal received by the drive signal supply circuit 19 in step S31 (step S32).

Then, the drive signal supply circuit 19 executes the intensity adjustment processing of the image forming laser beam in which current values corresponding to the respective drive signals 21r, 21g, 21b are adjusted based on the information on the actually radiated intensity obtained in step S32 (step S33), and returns the processing to the main processing. That is, the intensity of the image forming laser beam is adjusted such that the image forming laser beam obtains the preset intensity at the position of the light detection part 57.

In this manner, the RSD 1 according to this embodiment is operated in accordance with the above-described flow.

Finally, the above-mentioned respective embodiments merely constitute examples of the present invention and the present invention is not limited to these embodiments. Accordingly, it is needless to say that various modifications are conceivable depending on designs or the like without departing from the technical concept of the present invention even when the modifications are not included in the above-mentioned embodiments.

What is claimed is:

1. A retinal scanning display comprising:
   a light source part which is configured to radiate a laser beam having intensity corresponding to a drive signal which contains an image signal;
   a scanning part which is configured to scan the laser beam radiated from the light source part in two dimensional directions;
   a projection part which is configured, at image forming time, to project the laser beam which is radiated from the light source part and is scanned by the scanning part on a retina of an eye of a viewer thus projecting an image on the retina;
   a light detection part which is arranged at a position on which the laser beam which is radiated from the light source part and is scanned by the scanning part is incident at timing detection time for detecting scanning timing of the scanning part other than at the image forming time; and
   a light blocking part which is arranged between the scanning part and the viewer and is configured to block a laser beam which is scanned by the scanning part and advances toward the eye of the viewer at the timing detection time; and
   a control part which is configured to control the radiation of the laser beam from the light source part based on the detected timing of the laser beam by the light detection part, wherein
   the control part is configured to allow the light source part to radiate the laser beam at the timing detection time with intensity which exceeds a maximum value of intensity of the laser beam which is radiated from the light source part at the image forming time.

2. The retinal scanning display according to claim 1, wherein the light detection part is configured to output a detection signal corresponding to the laser beam incident on the light detection part, and
   the control part is configured to set the intensity of the laser beam radiated from the light source part at the timing detection time to a proper level regulated based on specification of the light detection part.

3. The retinal scanning display according to claim 1, wherein the control part is configured to set the intensity of the laser beam radiated from the light source part at the timing detection time to a value equal to or lower than a safety value for ensuring safety of the eye of the viewer.

4. The retinal scanning display according to claim 1, wherein the control part comprises:
  a first drive part which is configured to generate an image signal for radiating the laser beam from the light source part at the image forming time and to output the image signal to the light source part; and
  a second drive part which is configured to generate a timing detection drive signal for radiating the laser beam from the light source part at the timing detection time and to output the timing detection drive signal to the light source part, and
  the control part is configured to output the image signal and the timing detection drive signal to the light source part in a switchable manner or in a combined manner.

5. The retinal scanning display according to claim 1, wherein the light source part includes a red laser beam source which radiates a red laser beam, a blue laser beam source which radiates a blue laser beam and a green laser beam source which radiates a green laser beam, and is configured to radiate the laser beam in such a manner that intensity of the laser beam radiated from the laser beam source of each color as a laser beam to be radiated at the image forming time is modulated corresponding to the drive signal of each color containing the image signal, and
  the control part is configured to radiate the laser beam from the laser beam source of the color whose detection sensitivity detected by the light detection part is highest among the respective colors at the timing detection time.

6. The retinal scanning display according to claim 5, wherein the laser of the color whose detection sensitivity is highest in the light detection part is the red laser beam source.

7. The retinal scanning display according to claim 5, wherein the light source part includes an intensity detector which detects respective intensities of the radiated laser beams of respective colors, and
  the control part includes, in addition to a timing adjustment mode where the control part controls the radiation of the laser beam from the light source part based on the detected timing of the laser beam radiated from the light source part by the light detection part at the timing detection time, an intensity adjustment mode where the laser beams of the respective colors set to the intensities of maximum values are radiated from the light source part at timing different from the timing detection time and the image forming time, the intensities of the laser beams of the respective colors are detected by the intensity detector, and the intensities of the laser beams are adjusted, and the timing adjustment mode and the intensity adjustment mode are executed in a switchable manner at predetermined timing.

8. The retinal scanning display according to claim 1, wherein the scanning part comprises: a first optical scanning element which includes a reflection mirror which reflects a laser beam and is configured to scan the laser beam in a first direction in a reciprocating manner by swinging the reflection mirror; and a second optical scanning element which is configured to scan the laser beam in a second direction approximately orthogonal to the first direction.

* * * * *